United States Patent
Shao et al.

(10) Patent No.: US 9,056,207 B2
(45) Date of Patent: Jun. 16, 2015

(54) BIPHASIC DEFIBRILLATION CIRCUIT AND DEFIBRILLATOR

(75) Inventors: Ancen Shao, Shenzhen (CN); Saixin Zhou, Shenzhen (CN); Min An, Shenzhen (CN)

(73) Assignee: SHENZHEN MINDRAY BIO-MEDICAL ELECTRONICS CO., LTD, Shenzhen (CN)

( * ) Notice: Subject to any disclaimer, the term of this patent is extended or adjusted under 35 U.S.C. 154(b) by 0 days.

(21) Appl. No.: 13/328,661

(22) Filed: Dec. 16, 2011

(65) Prior Publication Data

US 2012/0158073 A1  Jun. 21, 2012

(30) Foreign Application Priority Data

Dec. 16, 2010 (CN) .......................... 2010 1 0592250

(51) Int. Cl.
*A61N 1/39* (2006.01)
(52) U.S. Cl.
CPC .................................... *A61N 1/3912* (2013.01)
(58) Field of Classification Search
USPC ............................................................ 607/5
See application file for complete search history.

(56) References Cited

U.S. PATENT DOCUMENTS

| | | | |
|---|---|---|---|
| 4,800,883 A * | 1/1989 | Winstrom | 607/7 |
| 5,411,525 A * | 5/1995 | Swanson et al. | 607/5 |
| 5,833,712 A * | 11/1998 | Kroll et al. | 607/7 |
| 2006/0122655 A1* | 6/2006 | Greatbatch | 607/33 |
| 2006/0129192 A1* | 6/2006 | Greatbatch et al. | 607/5 |

FOREIGN PATENT DOCUMENTS

| | | | | |
|---|---|---|---|---|
| CN | 1249695 A | 4/2000 | | |
| CN | 101443075 A | 5/2009 | | |
| CN | 101745179 A | 6/2010 | | |
| CN | 101745180 A | 6/2010 | | |
| DE | 202004016350 U1 | 3/2005 | | |
| EP | 0553863 A2 | 4/1993 | | |
| EP | 553863 A2 * | 8/1993 | | A61N 1/39 |
| EP | 0553863 B1 * | 8/1993 | | A61N 1/39 |
| EP | 1093829 A1 * | 4/2001 | | A61N 1/39 |

* cited by examiner

*Primary Examiner* — Carl H Layno
*Assistant Examiner* — Erin Piateski
(74) *Attorney, Agent, or Firm* — Kory D. Christensen; Stoel Rives LLP

(57) ABSTRACT

At least two energy storage devices are used to realize biphasic defibrillation therapy. One of the energy storage devices is the primary energy storage device and the other (e.g. second) energy storage device is the auxiliary energy storage device. The first energy storage device is used to implement both the first and second phase pulses of biphasic pulse therapy to the patient, and the second energy storage device can be used to assist in the first and/or second phase pulse. In other words, the second energy storage device may be combined with the first energy storage device to discharge electricity to the patient to realize the first and/or second phase pulse.

16 Claims, 8 Drawing Sheets

BIPHASIC DEFIBRILLATION CIRCUIT AND DEFIBRILLATOR

CROSS-REFERENCE TO RELATED APPLICATIONS

This application claims the benefit of Chinese Patent Application No. 201010592250.0, filed Dec. 16, 2010, which is incorporated herein by reference in its entirety.

TECHNICAL FIELD

The present disclosure relates to defibrillators.

SUMMARY OF THE INVENTION

Disclosed herein are embodiments of a biphasic defibrillation circuit applied to defibrillators.

DETAILED DESCRIPTION

According to statistics, more and more people lose their lives to heart attacks that have not been effectively and timely treated. Ventricular fibrillation, in which the ventricles lose the ability to supply blood and cannot pump a sufficient amount of blood, is one of the greatest threats to human life. According to medical research, the most effective treatment for ventricular fibrillation is defibrillation, which uses a large current pulse to stimulate the ventricles to return to their normal state.

Current automated external defibrillators use biphasic pulses to defibrillate a patient. Using biphasic pulses, the polarization effect will be generated when the heart is shocked by the first phase biphasic pulse. The second phase biphasic pulse wave can make heart cells shocked by the first phase biphasic depolarized thereby provide better treatment.

Figure 1:
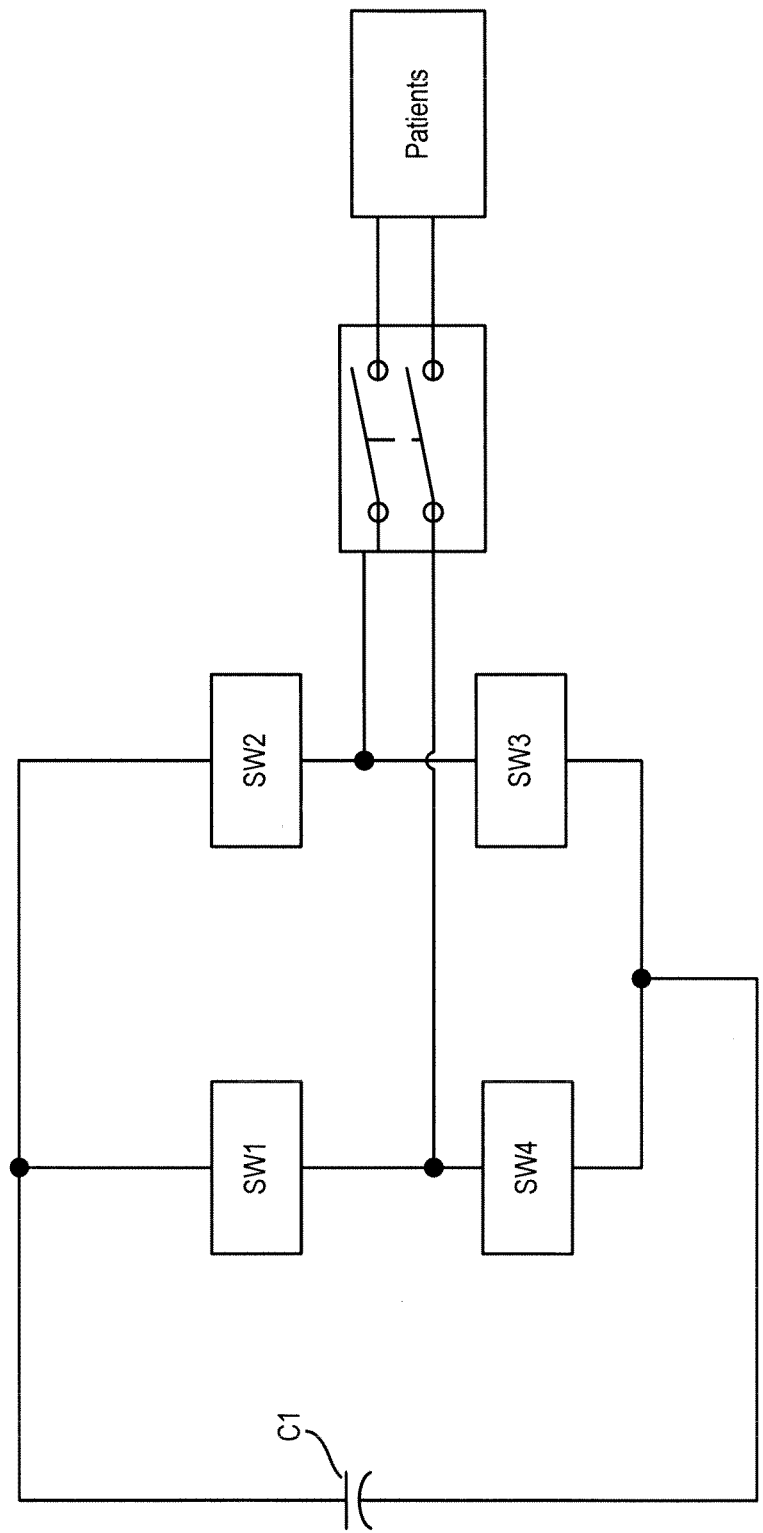
FIG. 1 is a schematic diagram of a biphasic defibrillation circuit including one capacitor.

As shown in FIG. 1, the biphasic circuit includes a capacitor and a switching circuit. When the switches SW1 and SW3 are turned on, the capacitor C1 discharges electricity to the patient to achieve the first phase of pulse therapy. When the switches SW2 and SW4 are turned on, the remaining energy of the capacitor C1 may be used to achieve the second phase of pulse therapy. The biphasic pulse is supplied by the same capacitor and the second phase pulse uses the remaining energy of capacitor C1 after the first phase of pulse therapy. Accordingly, the current flowing through the patient during the second phase pulse is significantly less than the current flowing through the patient during the first phase pulse. Especially for patients with small thoracic impedance resistance, the current of the second phase pulse is significantly smaller than the current of the first phase pulse, reducing the therapeutic effect.

Figure 2:
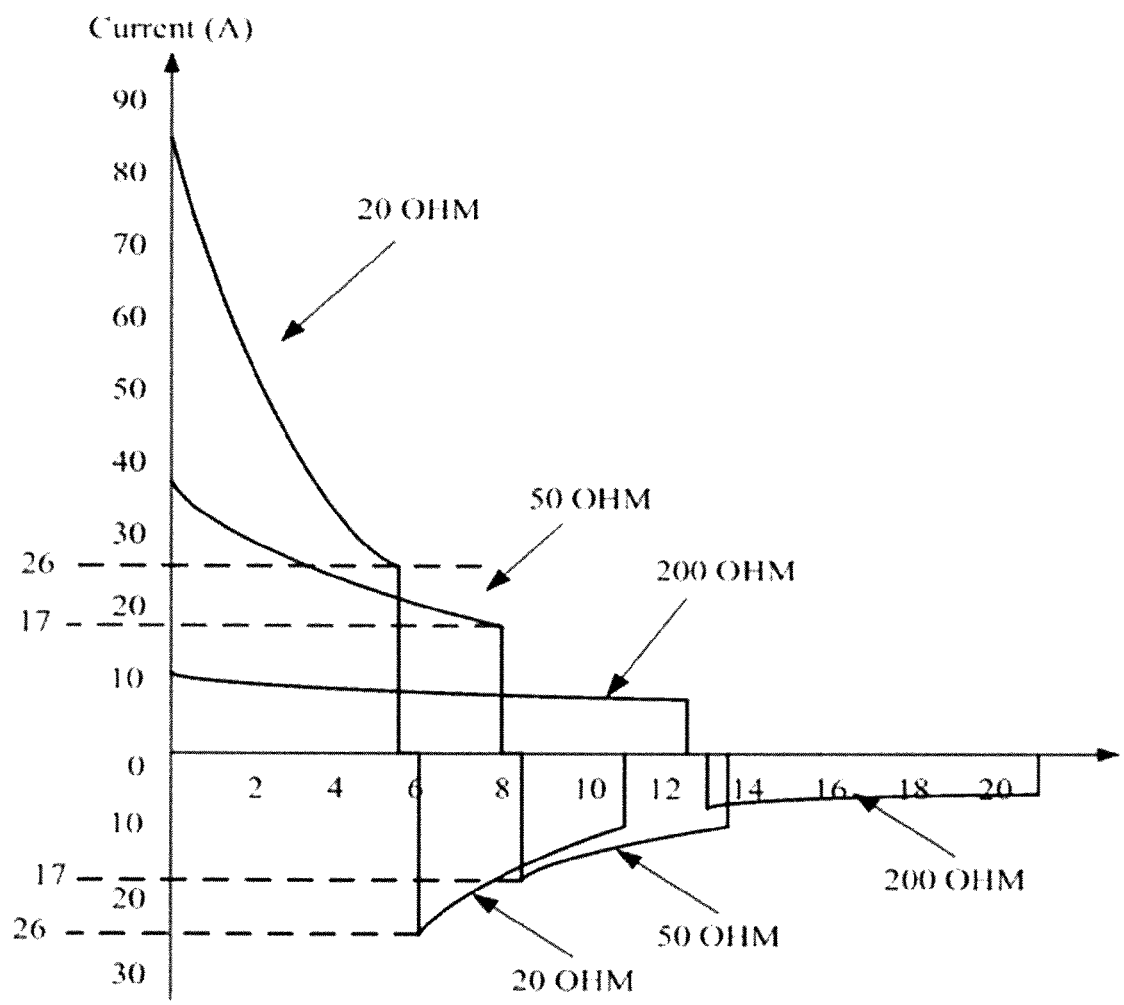
FIG. 2 is a graph of current waveforms flowing through patients with different thoracic impedance resistances.

FIG. 2 is a graph of a current waveform flowing through patient when discharging electricity. The biphasic pulse has two discharge stages: the first phase and the second phase. The polarity of the second phase current is opposite to the polarity of the first phase. The widely used biphasic pulse is biphasic truncated exponential (BTE) waveform shown in FIG. 2, one feature of which is that the initial current of the second phase pulse equals the end current of the first phase pulse. From FIG. 2, it can be observed that the difference between the current of the second phase pulse and the first phase pulse is small in patients with large impedance, and the difference can reach 5 times in patients with small thoracic impedance. As there is only one capacitor discharging electricity, the time constant of the body discharging electricity is the same.

The present disclosure is directed to a biphasic defibrillation circuit and a defibrillator, which are capable of producing biphasic pulses to defibrillate patients.

When patients need to be treated with defibrillation, biphasic defibrillation methods are generally adopted. That is, the first phase pulse is initially applied to the patient, after which the second phase pulse in the opposite direction to the first phase pulse is applied to the patient. For example, suppose the first phase pulse is a positive pulse and the second phase pulse is the opposite pulse. The switching state can be selectively changed by switching circuits, so the first and second phase pulse can be applied to defibrillation electrodes in turn.

In one embodiment, at least two energy storage devices are used to realize biphasic defibrillation therapy. One of the energy storage devices is the primary energy storage device and the other (e.g., second) energy storage device is the auxiliary energy storage device. The first energy storage device is used to implement both the first and second phase pulses of biphasic pulse therapy to the patient, and the second energy storage device can be used to assist in the first and/or second phase pulse. In other words, the second energy storage device may be combined with the first energy storage device to discharge electricity to the patient to realize the first and/or second phase pulse.

In one embodiment, the biphasic defibrillation circuit includes two energy storage devices. The first energy storage device is used to deliver the first phase pulse current to defibrillation electrodes during the first phase pulse and the second phase pulse current in the opposite direction relative to the first phase pulse current during the second phase pulse. The second energy storage device is used to deliver only the first phase pulse current to the defibrillation electrodes during the first phase pulse, or only the second phase pulse current during the second phase pulse, or both the first and second phase pulse current during the first and second phase pulses. When the second energy storage device is combined with the first energy storage device to deliver the first or second phase pulse current to the defibrillation electrodes, the second phase discharging time constant is different from the first phase discharging time constant or the starting voltage/current of the second phase pulse is larger than the ending voltage/current of the first phase pulse.

The second phase pulse discharging time constant is different from the first phase pulse discharging time constant, or the starting voltage of the second phase pulse is larger than the ending voltage of the first phase pulse.

In one embodiment, the first and second energy storage devices may be configured such that only the first energy storage device is used to deliver the first phase pulse current to the defibrillation electrodes during the first phase pulse of the biphasic pulse, and both the first and second energy storage devices are used to deliver the second phase pulse. For example, the first energy storage device may be connected with the second energy storage device in series or parallel to deliver the second phase pulse current to the defibrillation electrodes during the second phase pulse.

In one embodiment, the first energy storage device is connected with the second energy storage device serially. The first energy storage device is coupled to the defibrillation electrodes by the switching circuit during the first phase pulse, and the serially connected first and second energy storage devices are coupled to defibrillation electrodes by the switching circuit during the second phase pulse. For example, the switching circuit may include a first switching set and a second switching set. The first switching set may be turned on during the first phase pulse, so the positive and negative ends of the first energy storage device are coupled to the first and second output terminals of the switching circuit. The second switching set is turned on during the second phase pulse, so the positive and negative ends of the serially connected first and second energy storage devices, such as the positive end of the second energy storage device and the negative end of the first energy storage device, are coupled to the first and second output terminals of the switching circuit.

Because both the first and the second energy storage devices are used to deliver the second phase pulse, so the connection method of the first and second energy storage device can be configured to achieve a initial voltage or current of the second phase pulse that is larger than the ending voltage or current of the first phase pulse. This effectively avoids the shortcomings of existing approaches in which the initial current of the second phase pulse is much smaller than the initial current of the first phase pulse. By making discharging time constants and waveforms different between the first and second phase pulses, the probability of patient recovery is improved.

During the second phase of pulse therapy, the initial current of the second phase pulse can be adjusted to be larger than the ending current of the first phase pulse to decrease the difference between the first and second phase pulse current. This avoids the problem of the initial current of the second phase pulse being too small in the case of patients with low impedance. Thus, the therapeutic effect of the second phase pulse can be improved.

In another embodiment, both the first and second energy storage devices are used to deliver the first phase pulse current to the defibrillation electrodes during the first phase pulse, and only the first energy storage device is used to deliver the second phase pulse. For example, the first and second energy storage devices may be connected serially or in parallel to deliver the first phase current to the defibrillation electrodes during the first phase pulse, and only the first energy storage device is used to deliver the second phase pulse.

In yet another embodiment, the first and second energy storage devices are connected in the first combination method to deliver the first phase pulse current to the defibrillation electrodes during the first phase pulse, and the first and second energy storage device are connected in the second combination method to deliver the second phase pulse.

Figure 3:
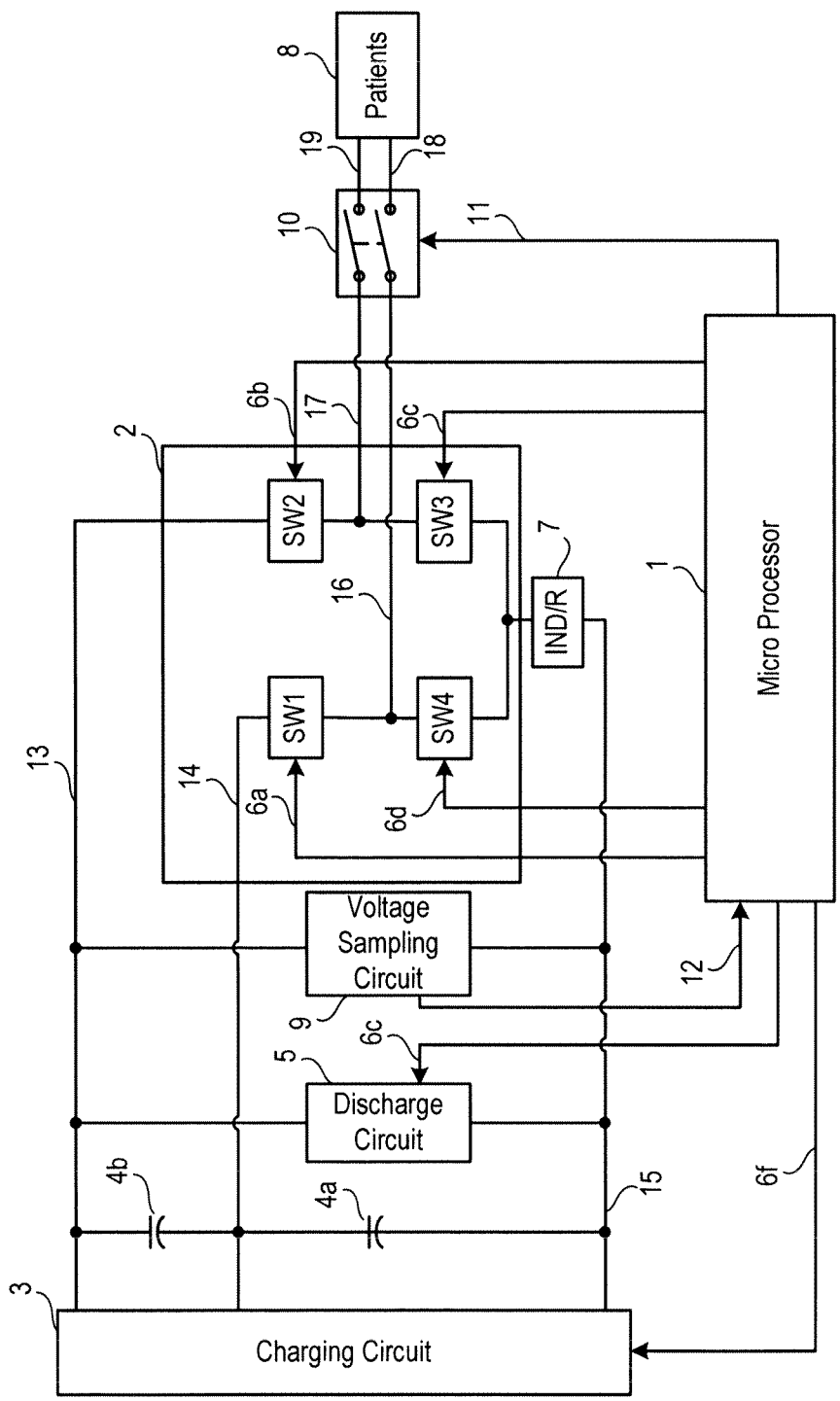
FIG. 3 is schematic diagram of a defibrillator.

As shown in FIG. 3, the defibrillator may include two defibrillation electrodes 18, 19 and a biphasic defibrillation circuit. The defibrillation electrodes 18, 19 are used to contact certain body parts. The biphasic defibrillation circuit may include a microprocessor 1, a switching circuit 2, a first energy storage device, and a second energy storage device.

In one embodiment, the microprocessor 1 is used as the control system of the biphasic defibrillation circuit. For example, the microprocessor 1 generates control commands according to user instructions, or it processes input data and generates control commands according to the processing result. In another embodiment, the microprocessor 1 may also be used as the control system of the defibrillator. As used herein, the term "microprocessor" may be used to generally refer to a number of different control devices, such as microcontrollers, FPGAs, etc.

The switching circuit 2 may selectively switch the switching state, so that the first and second phase pulses are applied to the defibrillation electrodes. The switching circuit 2 may include a first output terminal and a second output terminal connected to the defibrillation electrodes 18, 19, respectively. In one embodiment, the first and second output terminals are fixedly connected to the corresponding defibrillation electrodes 18, 19. However, in another embodiment, the first and second output terminals are removably connected to the corresponding defibrillation electrodes 18, 19 through an interface.

In one embodiment, the switching circuit 2 comprises a first switching set and a second switching set. The first switching set may include a first switch SW1 and a third switch SW3, and the second switching set may include a second switch SW2 and a fourth switch SW4. In one embodiment, control terminals of the four switches are coupled to the microprocessor 1. The four switches respond to control signals outputted by the microprocessor 1 to switch between on and off states. In other embodiments, the switching circuit 2 may also include driving circuits corresponding to the four switches, respectively, and the control terminals of the four switches may be coupled to the corresponding driving circuits.

In one embodiment, the first and second energy storage devices are capacitors, as shown in FIG. 3. However, a skilled artisan will recognize that other types of energy storage devices can be used, such as batteries. The first energy storage device may include a first capacitor 4a, and the second energy storage device may include a second capacitor 4b. It will be understood by a skilled artisan that the first capacitor 4a and the second capacitor 4b can be a single capacitor or can be a combination of multiple capacitors.

As shown in FIG. 3, the first capacitor 4a and the second capacitor 4b may be connected serially. That is, the first lead 14 of the first capacitor 4a is connected to the second lead of the second capacitor 4b. For purposes of description, the disclosure will refer to three leads, which are the first lead 13 of the second capacitor 4b, the first lead 14 of the first capacitor 4a, and the second lead 15 of the first capacitor 4a. The first switch SW1 is coupled between the lead 14 and the first output terminal 16 of the switching circuit. The second switch SW2 is coupled between the first lead 13 of the second capacitor 4b and the second output terminal 17 of the switching circuit. The third switch SW3 is coupled between the second lead 15 of the first capacitor 4a and the second output terminal 17 of the switching circuit. The fourth switch SW4 is coupled between the second lead 15 of the first capacitor 4a and the first output terminal 16 of the switching circuit.

During the first phase of the biphasic pulse, the first switch SW1 and the third switch SW3 are turned on, so the first lead 14 and the second lead 15 of the first capacitor 4a are coupled to the first output terminal 16 and the second output terminal 17. When the first output terminal 16 and the second output terminal 17 connect with the defibrillation electrodes 18, 19 that contact with the patient, the first capacitor 4a discharges electricity, producing the first phase pulse. For purposes of description, it is assumed that the first phase pulse current is in the positive direction. After the first phase pulse, the first switch SW1 and the third switch SW3 are turned off, and the first capacitor 4a terminates discharging.

During the second phase of the biphasic pulse, the second switch SW2 and the fourth switch SW4 are turned on, so the first lead 13 of the second capacitor 4b and the second lead 15 of the first capacitor 4a are coupled to the second output terminal 17 and the first output terminal 16. The serially connected first capacitor 4a and second capacitor 4b discharge electricity, producing the second phase pulse. The second phase pulse current is in the opposite direction of the first phase pulse current. After the second phase pulse, the second switch SW2 and the fourth switch SW4 are turned off, and the first capacitor 4a and the second capacitor 4b terminate discharging.

In one embodiment, the first capacitor 4a provides the first phase pulse to the defibrillation electrodes during the first phase pulse, and the serially connected first capacitor 4a and second capacitor 4b provide the second phase pulse to the defibrillation electrodes 18, 19 during the second phase pulse. The initial voltage of the second phase pulse is equal to the surplus voltage of the first capacitor 4a after the first phase discharge plus the initial discharging voltage of the second capacitor 4b, so the initial discharging voltage/current is larger than the ending voltage/current of first phase pulse.

Figure 4:
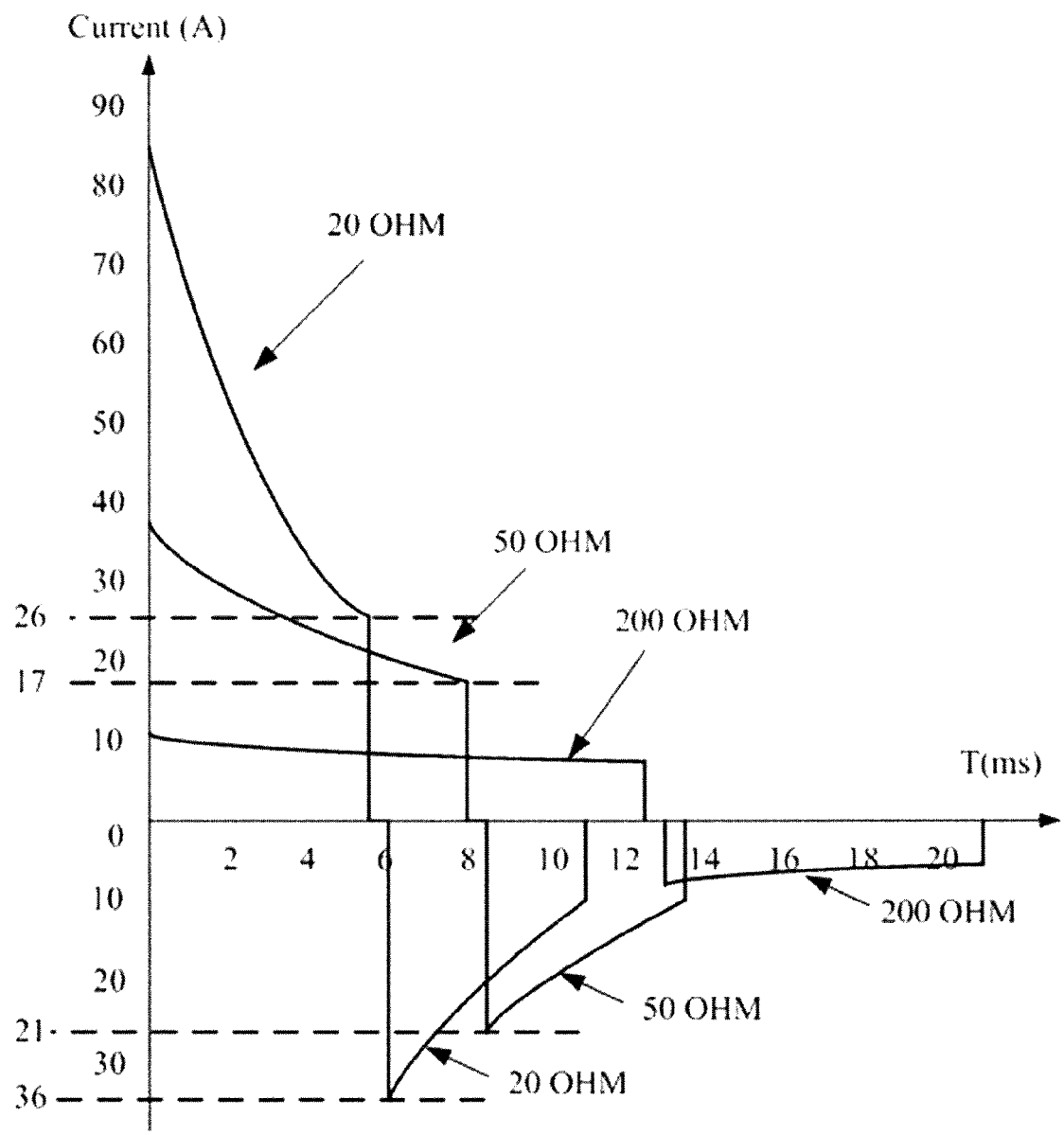
FIG. 4 is a graph of current waveforms flowing through patients with different thoracic impedance resistances.

FIG. 4 illustrates the biphasic current comparison according to different thoracic impedances. When the thoracic impedance is 20 OHM, the initial current of the second phase pulse is 36 A, which is larger than the ending current of the first phase pulse of 26 A.

In one embodiment, the first capacitor 4a is a high voltage capacitor, so the first capacitor 4a has a larger volume and relatively high cost. However, the second capacitor 4b may have a large capacitance and a low voltage. In one embodiment, the voltage of the second capacitor 4b may even be ⅒th of the first capacitor 4a. Accordingly, the second capacitor 4b may have a small volume and a lower cost. In this embodiment, only the first capacitor needs to be a large capacitor, decreasing the volume, weight, and cost of the defibrillator.

In another embodiment, as shown in FIG. 3, the biphasic defibrillation circuit may further include a charging circuit 3, with one output terminal of the microprocessor 1 coupled to the charging circuit 3. The charging circuit 3 receives a control signal sent from the microprocessor and charges the first and second energy storage devices to a desired voltage.

Figure 5:
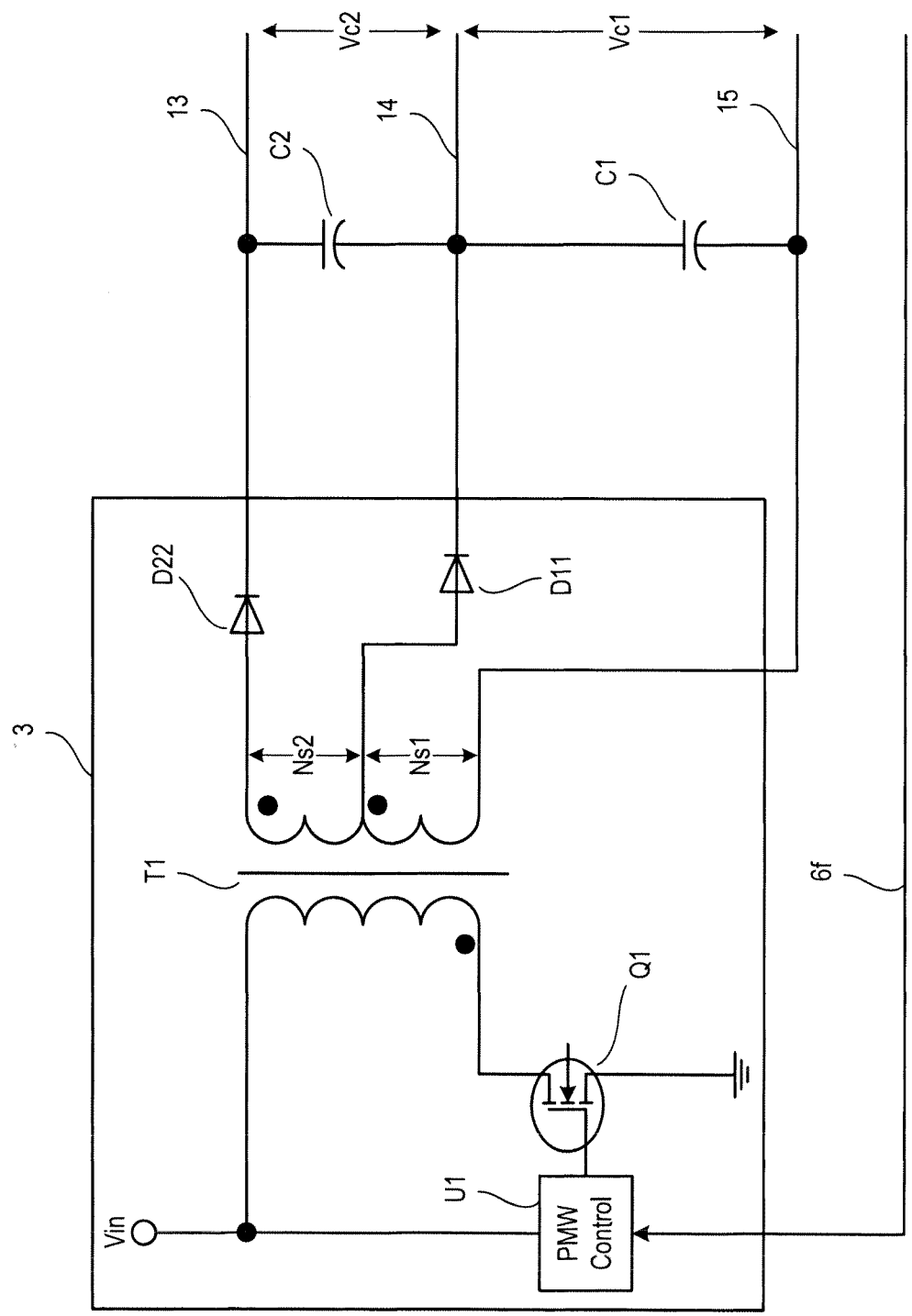
FIG. 5 is a circuit diagram of the charging circuit shown in FIG. 3.

In one embodiment, as shown in FIG. 5, the charging circuit includes a pulse-width modulation (PWM) control U1, a fifth switch Q1, and a transformer T1. One end of the PWM control U1 may be coupled to the microprocessor 1, and the other end may be coupled to the control terminal of the fifth switch Q1. PWM control U1 responds to control signals sent from the microprocessor 1 by the control line 6f and controls the fifth switch Q1 switching between off and on states. The transformer comprises a primary coil and at least an auxiliary coil. The primary coil is coupled between the power and the ground through the fifth switch, and the two terminals and center tap of the auxiliary coil form a three-terminal charging structure, which can charge the first and second energy storage devices quickly. Such a charging circuit may control the charging voltage applied to the two energy storage devices by adjusting the position of the center tap, so that the charging voltage applied to the two energy storage devices may be the same or a certain ratio.

An embodiment of the defibrillation circuit is shown in FIG. 3. When the charging circuit charges the first and second energy storage devices, the connection is shown in FIG. 5. The first terminal of the primary coil is coupled to the power Vin, and the second terminal of the primary coil is coupled to the ground through the fifth switch Q1. Two terminals of the auxiliary coil are coupled to the second lead 15 of the first energy storage device C1 and the first lead 13 of the second energy storage device C2 through one diode, and the center tap of the auxiliary coil is coupled to the first lead 14 of the first energy storage device through one diode.

The fifth switch Q1 may control the primary coil power on or off, so it may be coupled between the power Vin and primary coil in other embodiments.

The fifth switch Q1 may be a MOSFET or other types of controllable switches, such as a transistor, an electronic switch, and so on. The transformer may be an isolated flyback transformer in some embodiments.

When the first energy storage device C1 and the second energy storage device C2 need to be charged, the microprocessor 1 may send a control signal to start the PWM controller U1 through the control line 6f, so the fifth switch Q1 is turned on and the flyback converter circuit charge the energy storage device C1 and C2. The charging voltage ratio of the first energy storage device C1 to the second energy storage devices C2 equals the turns ratio of isolate winding NS1 to NS2. That is:

$$Vc1:Vc2=Ns1:Ns2$$

When the charging voltage of the first energy storage device C1 and second energy storage device C2 reaches the desired voltage, the microprocessor 1 stops the PWM controller U1 through the control line 6f and the flyback converter circuit stops electrifying the first energy storage device C1 and second energy storage device C2.

In another embodiment, the charging circuit 3 does not include a PWM controller U1, and the fifth switch Q1 switches off or on according to control signals sent from the microprocessor 1.

In one embodiment, the charging circuit does not need to adjust the voltage ratio of the first energy storage device C1 to the second energy storage device C2 by detecting the voltage of the first energy storage device C1 and the second energy storage device C2. The charging ratio of the first energy storage device C1 to the second energy storage devices C2 may be changed by adjusting the position of the center tap, simplifying circuit construction.

In another embodiment, as shown in FIG. 3, the biphasic defibrillation circuit may further include a self-discharge circuit 5 and a voltage sampling circuit 9. The voltage sampling circuit 9 samples the voltage of the serially connected first capacitor 4a and second capacitor 4b and lowers it to the microprocessor-acceptable level range, after which the voltage sampling circuit 9 outputs the sampled voltage to the microprocessor through the line 12. The self-discharge circuit 5 is coupled between the second lead 15 of first capacitor 4a and the first lead 13 of second capacitor 4b, and is used to discharge excess energy stored in the first capacitor 4a and second capacitor 4b under a control signal outputted by the microprocessor through control line 6e after the biphasic pulse.

A discharge protection circuit 7 with an inductance or a resistance feature is coupled between the second lead 15 of first capacitor 4a, the third switch SW3, and the fourth switch SW4. The inductance feature can effectively limit the instant start discharge current raise rate, and the resistance feature can limit the current during defibrillation discharging.

In one embodiment, a relay is provided between two output terminals of the switching circuit and the pair of defibrillation electrodes 18, 19, and the microprocessor turns the relay on or off through the control line 11.

In one embodiment, the defibrillator treats patients through three steps: the charge phase, the discharge and shock phase, and the energy self-discharge phase.

Step 1, the charge phase. The microprocessor 1, as a control system, receives energy selection command and charge command from a user and controls the charging circuit 3 to start charging the first capacitor 4a and second capacitor 4b through a control signal. In the meantime, the microprocessor 1 monitors the charging voltage of the first capacitor 4a and the second capacitor 4b through the voltage sampling circuit 9, and the microprocessor 1 outputs a control signal to stop the charging circuit 3 from charging the first capacitor 4a and the second capacitor 4b.

Step 2, the discharge and shock phase. After the charge phase, the microprocessor 1 waits for a discharge and shock command from a user, after which the defibrillator implements biphasic shock treatment to a patient. First, the microprocessor 1 closes the relay 10 through the control line 11, so patient 8 connects with the switching circuit 2 through the defibrillation electrodes 18, 19, and the first and second output terminals 16, 17. The microprocessor 1 then turns on the first switch SW1 and third switch SW3 through the control lines 6a and 6c, and the first phase pulse current coming from the positive pole of the first capacitor 4a flows through the first lead 14, the first switch SW1, the first output terminal 16, the relay 10, the defibrillation electrode 18, the patient 8, the defibrillation electrode 19, the relay 10, the second output terminal 17, the third switch SW3, the protection circuit 7, and the second lead 15 of the first capacitor 4a to the negative pole of the first capacitor 4a. The direction of current flowing through the patient is from the defibrillation electrode 18 to the defibrillation electrode 19, which is defined as positive for this example. After the first phase discharge, the microprocessor 1 turns off the first switch SW1 and the third switch SW3 through the control lines 6a and 6c.

After a short time delay (e.g., 0.5 ms), the microprocessor 1 turns on the second switch SW2 and fourth switch SW4 through the control lines 6b and 6d. The second phase current coming from the positive pole of the second capacitor 4b flows through the second switch SW2, the second output terminal 17, the relay 10, defibrillation electrode 19, the patient 8, the defibrillation electrode 18, the relay 10, the first output terminal 16, the fourth switch SW4, the protection circuit 7, and the second lead 15 of the first capacitor 4a to the negative pole of the first capacitor 4a. The direction of current flowing through the patient is from the defibrillation electrode 19 to the defibrillation electrode 18, which is defined as negative for this example. After the second phase discharge, the microprocessor 1 turns off the second switch SW2 and the fourth switch SW4 through the control lines 6a and 6c.

The serially connected first capacitor 4a and second capacitor 4b implement treatment to the patient by discharge and shock during the second phase pulse.

After the second phase discharge, the relay 10 is disconnected by microprocessor 1 through the control line 11, and the biphasic pulse has been sent.

Step 3, the residual energy self-discharge phase. After the biphasic pulse has been sent, the microprocessor 1 turns on the energy discharge circuit through the control line 6e. Thus, the serially connected first capacitor 4a and second capacitor 4b discharge electricity through the energy self-discharge circuit.

Various modifications may be made to the circuit of FIG. 3. For example, the serially connected first and second energy storage devices may be used to deliver the first phase pulse current to the defibrillation electrodes during the first pulse, and only the first energy storage device delivers the second phase pulse current to the defibrillation electrodes during the second phase pulse. For example, the first and second capacitors 4a and 4b are connected serially, the first lead 13 of the first capacitor 4a is coupled to the first switch SW1, the first lead 14 of the second capacitor 4b is coupled to the second switch SW2, and the second lead 15 is coupled to the third and fourth switches SW3 and SW4. In such an embodiment, during the first phase pulse, the first capacitor 4a, the second capacitor 4b, the first switch SW2, the first output terminal 16, the second output terminal 17, and the third switch SW3 form a loop. During the second phase pulse, the first capacitor 4a, the second switch SW2, the second output terminal 17, the first output terminal 16, and the fourth switch SW4 form a loop.

In another embodiment, only the first energy storage device is used to deliver the first phase pulse current to the defibrillation electrodes during the first phase pulse, and the first and second energy storage devices are connected in parallel to deliver the second phase pulse current to the defibrillation electrodes during the second phase pulse. Specifically, the first and second energy storage devices are connected in parallel, the first energy storage device is coupled to the defibrillation electrodes by the switching circuit during the first phase pulse, and the first and second energy storage devices, connected in parallel, are coupled to the defibrillation electrodes during the second phase pulse. As an example, the first energy storage device includes a first capacitor 4a, and the second energy storage device comprises a second capacitor 4b.

Figure 6:
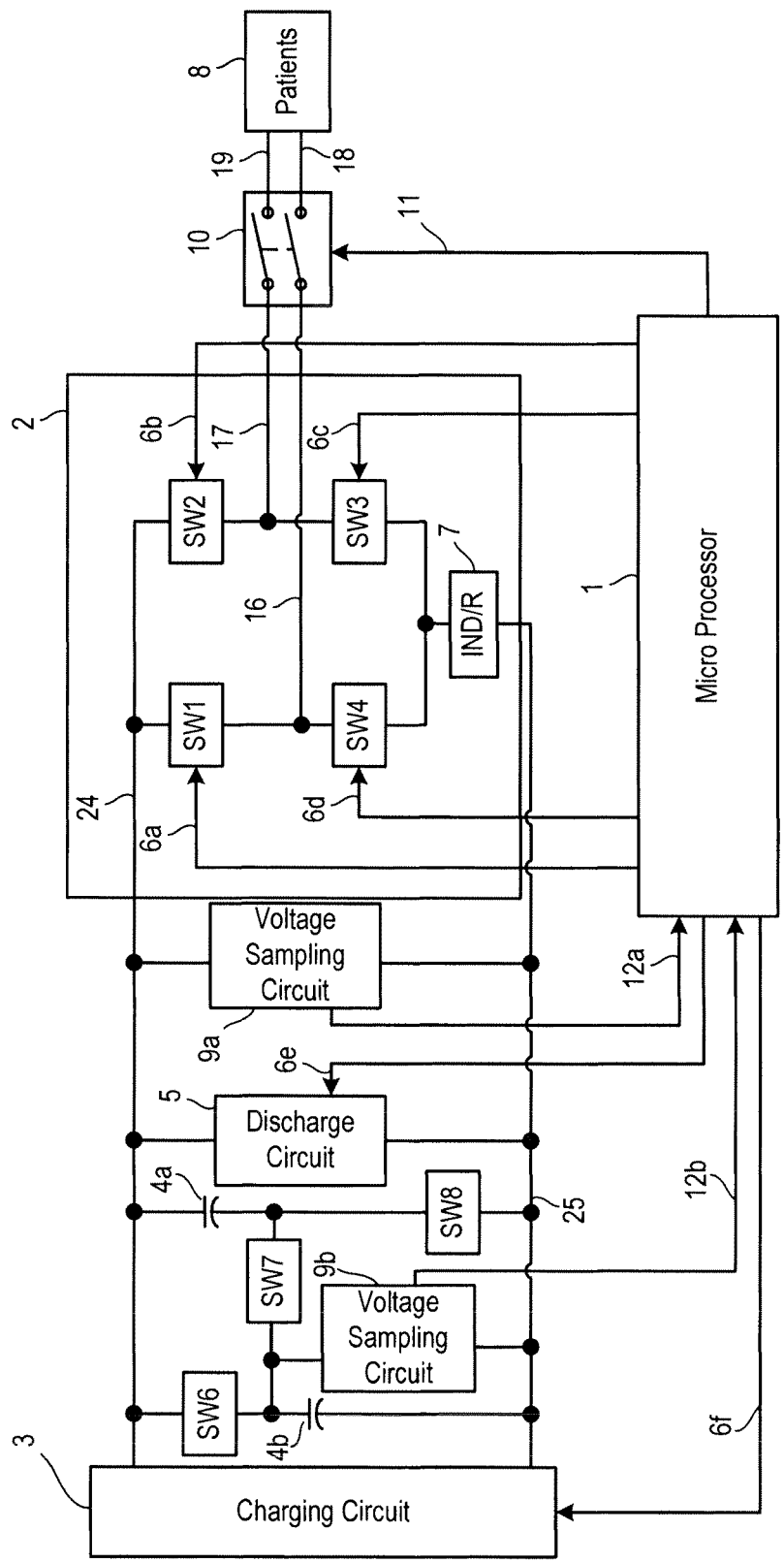
FIG. 6 is schematic diagram of a defibrillator.

As shown in FIG. 6, the biphasic defibrillation circuit structure is the same as the biphasic defibrillation circuit shown in FIG. 3, except the energy storage device is coupled to the charging circuit 3 and the switching circuit 2 in a different way. In this embodiment, the sixth switch SW6 and second capacitor 4b are connected serially, the sixth switch SW6 is turned off during the first phases pulse and is turned on during the second phase pulse by the microprocessor or other controller(s). The serial branch formed by the sixth switch SW6 and the second capacitor 4b connects the first capacitor 4a in parallel, thus realizing a parallel branch of the first and second energy storage device.

The switching circuit 2 comprises the first and second output terminals 16 (such as sternum leads) and 17 (such as apex lead) corresponding to defibrillation electrodes, and the first and second switch set. The first switch set are turned off during the second phase pulse and turned on during the first phase pulse, so the positive and negative terminals of the parallel branch are coupled to the first output terminal 16 and second output terminal 17. The second switch set are turned off during the first phase pulse and turned on during the second phase pulse, so the positive and negative terminals of the parallel branch are coupled to the second output terminal 17 and first output terminal 16. As shown in FIG. 6, the first switch set comprises the first switch SW1 and the third switch SW3, and the second switch set comprises the second switch SW2 and the fourth switch SW4. The first switch SW1 is coupled between the positive lead 24 of the parallel branch and the first output terminal 16 of the switching circuit, the second switch SW2 is coupled between the positive lead 24 and the second output terminal 17, the third switch SW3 is coupled between the negative lead 25 of the parallel branch and the second output terminal 17, and the fourth switch SW4 is coupled between the negative lead 25 and the first output terminal 16.

In one embodiment, the first capacitor 4a is the primary energy storage device, and the second capacitor 4b is the auxiliary energy storage device. During the first phase discharging, the switch SW6 is turned off, and only the first capacitor 4a implements the first phase discharge and shock treatment to the patient. During the second phase discharging, both the first capacitor 4a and the second capacitor 4b implement the second phase discharge and shock treatment to the patient. Thus, discharging time constants and waveforms are different between the first and second phase pulses. For example, because the first capacitor 4a is connected to the second capacitor 4b in parallel, the first capacitor 4a would be charged by the second capacitor 4b. Accordingly, the parallel branch voltage is higher than the first capacitor 4a voltage when the first phase discharge ends. Thus, the second phase initial current is larger than the first phase ending current.

As shown in FIG. 6, there is another way to realize discharging time constants are different between the first and second phase pulse. During the first phase pulse, the switch SW6 is turned on, and the parallel connected first capacitor 4a and second capacitor 4b implement the first phase discharge and shock treatment to the patient. During the second phase pulse, only the first capacitor 4a implements the second phase discharge and shock treatment to the patient. Because the first and second capacitors are connected in parallel during the first phase pulse, the discharging time constant of the first phase pulse is larger than the discharging time constant of the second phase pulse.

Figure 7:
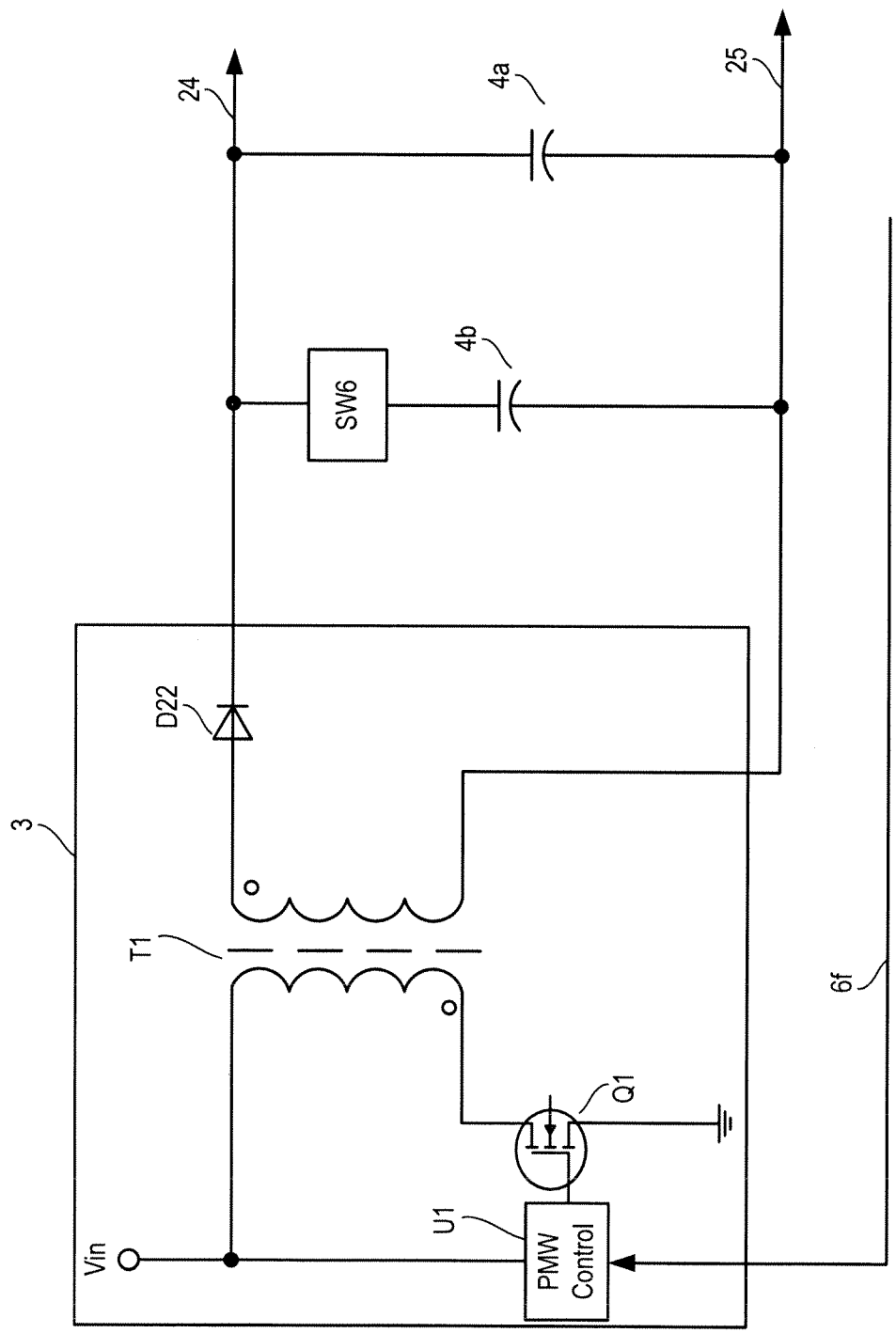
FIG. 7 is a circuit diagram of the charging circuit shown in FIG. 6.

Another embodiment of the structure of the charge circuit is shown in FIG. 7. The charge circuit comprises a fifth switch Q1 and a transformer T1. The primary coil of the transformer T1 is coupled between the source Vin and ground through the fifth switch Q1, and two terminals of the auxiliary coil are coupled to the positive lead 24 and negative lead 25 of the parallel branch.

The fifth switch Q1 is turned on by the microprocessor 1 during charging, so the first capacitor 4a and the second capacitor 4b are charged by the transformer T1. As shown in FIG. 6, the voltage sampling circuit 9 samples charging voltage of the second capacitor 4b and sends it to the microprocessor 1. The microprocessor 1 determines whether to turn off the fifth switch Q1 by charging voltage of the first capacitor 4a and the second capacitor 4b, so as to stop charging the first capacitor 4a and the second capacitor 4b. In addition, the microprocessor 1 may also determine whether to turn off the sixth switch SW6 by charging voltage of the second capacitor 4b, so as to stop charging the second capacitor 4b and continue charging the first capacitor 4a. Thus, the first capacitor 4a charge voltage is higher than the second capacitor 4b charge voltage, and the charge ratio of the first capacitor 4a to the second capacitor 4b can be controlled.

One terminal of the discharge circuit 5 is coupled to the positive lead 24 of parallel branch, and another terminal of the discharge circuit 5 is coupled to the negative lead 25 of the parallel circuit.

The external defibrillator shown in FIG. 6 includes three phases to implement treatment to the patient: the charge phase, the discharge and shock phase, and the self-discharge phase. However, the difference between it and the external defibrillator shown in FIG. 3 is as follows.

Step 1, the charge phase. The switch SW6, shown in FIG. 7, is turned on during the charge step, so the charging circuit 3 charges the first capacitor 4a and the second capacitor 4b connected in parallel. In another way, the switch SW6 is turned on for a period of time, such that the charging circuit 3 may charge the first capacitor 4a and second capacitor 4b connected in parallel. The switch SW6 then is turned off so the charging circuit 3 charges the first capacitor 4a only.

Step 2, the discharge and shock phase. Two discharge methods and discharge pulse features can be achieved by different control strategies of controller 1.

In the first method, the first capacitor 4a is the primary energy storage device and the second capacitor 4b is the auxiliary energy storage device. The switch SW6 is turned off during the first phase pulse discharge, such that the first capacitor 4a implements the first phase pulse discharge treatment to the patient. The switch SW6 is turned on during the second phase pulse discharge, such that the first capacitor 4a and second capacitor 4b are connected in parallel to implement the second phase pulse discharge treatment to the patient. Thus, a different discharge time constant and waveform are realized between the first and second phase pulses. For example, because the first capacitor 4a and second capacitor 4b are connected in parallel, the second capacitor 4b will charge the first capacitor 4a, so the second phase initial voltage is higher than the first phase ending voltage and the second phase initial current is larger than the first phase ending current.

According to a second method, the switch SW6 is turned on during the first phase pulse discharge, such that the first capacitor 4a and second capacitor 4b are connected in parallel to implement the first phase pulse discharge treatment to the patient. The switch SW6 is turned off during the second phase pulse discharge, such that only the first capacitor 4a implements the second phase pulse discharge treatment to the patient. Because the first capacitor 4a and the second capacitor 4b are connected in parallel during the first phase pulse discharge, the first phase discharge time constant is larger than the second phase discharge time constant.

Step 3, the residual energy self-discharge phase. The switch SW6 is turned on during the residual energy self-discharge phase, such that energy stored in the capacitors 4a and 4b can be discharged in parallel. This is different from the embodiment shown in FIG. 3.

Figure 8:
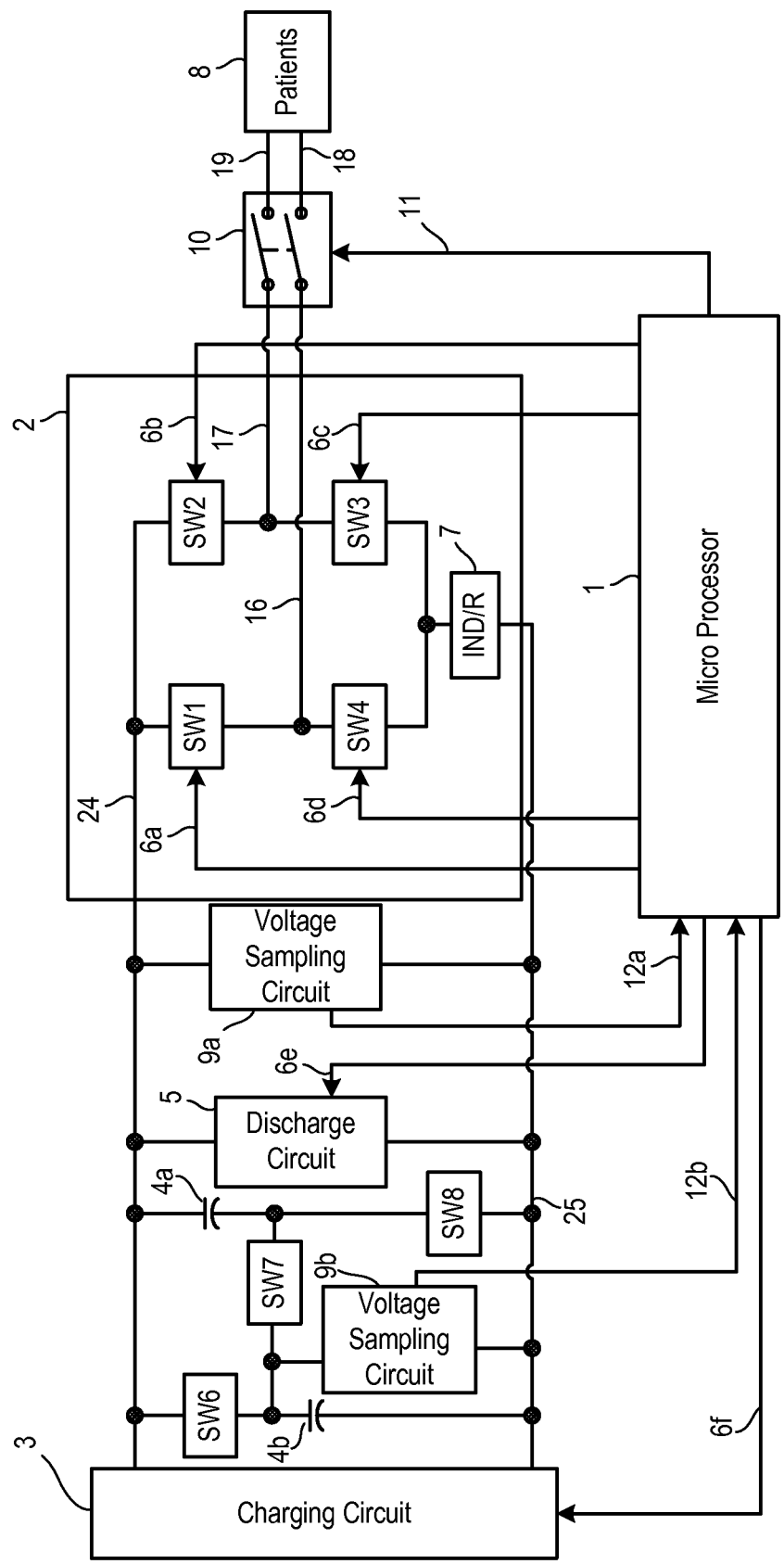
FIG. 8 is a schematic diagram of a defibrillator.

FIG. 8 illustrates another embodiment of a structure for a defibrillation circuit. The first energy storage device is the primary energy storage device, and the second energy storage device is the auxiliary energy storage device. In this embodiment, the first energy storage device comprises a first capacitor 4a, and the second energy storage device comprises a second capacitor 4b. The defibrillation circuit comprises a switching circuit 2, a first capacitor 4a, a second capacitor 4b, a sixth switch SW6, a seventh switch SW7, and an eighth switch SW8. The structure and control method of the switching circuit 2 is the same as the method of switching circuits in the abovementioned embodiments. The sixth switch SW6 connects the positive plate of the second capacitor 4b, and the eighth switch SW8 connects the negative plate of the first capacitor 4a. The first and second energy storage parallel branches comprise two serial branches. One serial branch is formed by the sixth switch SW6 and the second capacitor 4b, and another serial branch is formed by the eighth switch SW8 and the first capacitor 4a. The positive lead 24 of the parallel branch connects the first switch SW1 and second switch SW2, and the negative lead 25 of the parallel branch connects the third switch SW3 and fourth switch SW4. The seventh switch SW7 couples the negative plate of the second capacitor 4b and the positive plate of the first capacitor 4a. The microprocessor 1 controls the sixth switch SW6, the seventh switch SW7, and the eighth switch SW8 to realize various discharge modes described below.

In a first discharge mode, the sixth switch SW6 and the eighth switch SW8 are turned off and the seventh switch SW7 is turned on during the first phase pulse, such that the first capacitor 4a and the second capacitor 4b connected serially implement the first phase discharge and shock treatment to the patient. The sixth switch SW6 and the eighth switch SW8 are turned on and the seventh switch SW7 is turned off during the second phase pulse, such that the first capacitor 4a and the second capacitor 4b connected in parallel implement the second phase discharge and shock treatment to the patient.

In a second discharge mode, the sixth switch SW6 and the eighth switch SW8 are turned on and the seventh switch SW7 is turned off during the first phase pulse, such that the first capacitor 4a and the second capacitor 4b are connected in parallel to implement the first phase discharge and shock treatment to the patient; the sixth switch SW6 and the eighth switch SW8 are turned off and the seventh switch SW7 is turned on during the second phase pulse, such that the first capacitor 4a and the second capacitor 4b connected serially implement the second phase discharge and shock treatment to the patient.

In a third discharge mode, the eighth switch SW8 is turned on and the sixth switch SW6 and the seventh switch SW7 are turned off during the first phase pulse. Only the first capacitor 4a implements the first phase discharge and shock treatment to the patient, The sixth switch SW6 and the eighth switch SW8 are turned off and the seventh switch SW7 is turned on during the second phase pulse, such that the first capacitor 4a and the second capacitor 4b connected serially implement the second phase discharge and shock treatment to the patient. Alternatively, the sixth switch SW6 and the eighth switch SW8 are turned on and the seventh switch SW7 is turned off during the second phase pulse, such that the first capacitor 4a and the second capacitor 4b connected in parallel implement the second phase discharge and shock treatment to the patient.

In a fourth discharge mode, the sixth switch SW6 and the eighth switch SW8 are turned off and the seventh switch SW7 is turned on during the first phase pulse, such that the first capacitor 4a and the second capacitor 4b connected serially implement the first phase discharge and shock treatment to the patient. Alternatively, the sixth switch SW6 and the eighth switch SW8 are turned on and the seventh switch SW7 is turned off during the first phase pulse, such that the first capacitor 4a and the second capacitor 4b connected in parallel implement the first phase discharge and shock treatment to the patient. The eighth switch SW8 is turned on and the sixth switch SW6 and the seventh switch SW7 are turned off during the second phase pulse, such that only the first capacitor 4a implements the second phase discharge and shock treatment to the patient.

In the embodiment shown in FIG. 8, the methods of charging the first capacitor 4a and the second capacitor 4b, and detecting and controlling charge voltage are the same as the methods adopted in the embodiment shown in FIG. 6. In addition, the charging circuit may be the same as the circuit shown in FIG. 5. The first capacitor 4a and second capacitor 4b are coupled between the terminals and center tap of the auxiliary coil, respectively.

In the above mentioned embodiments, the first and second energy storage devices could be independent capacitors or combination capacitors. The combination capacitors could be serial, parallel, or hybrid capacitors, which could also comprise other devices, such as resistive devices. It will be understood by those having skill in the art that the first and second energy storage devices could be other energy storage devices, such as batteries, etc. When the first and second energy storage devices include batteries, the biphasic defibrillation circuit may not include charge circuits.

In the above mentioned embodiments, the switching circuit is controlled by the microprocessor. It can be understood by a skilled artisan that the state of the switching circuit can be also switched by other methods, such as manual control and hand trigger.

It will be understood by those having skill in the art that many changes may be made to the details of the above-described embodiments without departing from the underlying principles of the invention. The scope of the present invention should, therefore, be determined only by the following claims.

The claims following this written disclosure are hereby expressly incorporated into the present written disclosure, with each claim standing on its own as a separate embodiment. This disclosure includes all permutations of the independent claims with their dependent claims. Recitation in the claims of the term "first" with respect to a feature or element does not necessarily imply the existence of a second or additional such feature or element.

What is claimed is:

1. A biphasic defibrillation circuit for supplying a biphasic pulse to a patient when connected to defibrillation electrodes of an automated external defibrillator, comprising:

a switching circuit comprising a first switch, a second switch, a third switch, and a fourth switch, wherein a first output terminal and a second output terminal from the switching circuit are respectively coupled to the defibrillation electrodes, wherein a first phase pulse and a second phase pulse in an opposite direction to the first phase pulse are applied to the defibrillation electrodes by the switching circuit;

a first energy storage device coupled to the defibrillation electrodes by the switching circuit for delivering a first phase current to the defibrillation electrodes during the first phase pulse and delivering a second phase current in an opposite direction to the first phase current to the defibrillation electrodes during the second phase pulse, wherein the first energy storage device is a high voltage energy storage device, a first lead of the first energy storage device is coupled with the switching circuit directly and a second lead of the first energy storage device is coupled with the switching circuit through an eighth switch;

a second energy storage device coupled to defibrillation electrodes during at least one of the first and second phase pulses for respectively delivering at least one of the first phase current and the second phase current in conjunction with the first energy storage device, wherein the second energy storage device is a low voltage energy storage device, a first lead of the second energy storage device is coupled with the switching circuitry through a sixth switch and with the second lead of the first energy storage device through a seventh switch and a second lead of the second energy storage device is coupled with the switching circuit directly; and a charging circuit coupled to the first and second energy storage devices for charging the first and second energy storage devices, wherein charging of the first and second energy storage devices is controlled by a fifth switch;

wherein a serial branch formed by the sixth switch and the second energy storage device connects in parallel to a serial branch formed by the first energy storage device and the eighth switch; and wherein a difference between a first length of a first discharging time of the first phase pulse and a second length of a second discharging time of the second phase pulse is less than 40 percent of the first length of the first discharging time.

2. The biphasic defibrillation circuit according to claim 1, wherein only the first energy storage device delivers the first phase current during the first phase pulse, and both the first and second energy storage devices deliver the second phase current in the opposite direction of the first phase current during the second phase pulse.

3. The biphasic defibrillation circuit according to claim 2, wherein the first energy storage device connects with the second energy storage device in series through the seventh switch, and wherein the switching circuit comprises:
a first switch set, comprising the first switch and the third switch, wherein switches of the first switch set and the seventh switch are turned off and the sixth and eighth switches are turned on during the second phase pulse and the switches of the first switch set and the seventh switch are turned on and the sixth and eighth switches are turned off during the first phase pulse to make a positive and negative terminals of a serial branch formed by the first energy storage device, the seventh switch, and the second energy storage device couple to the first and second output terminals respectively; and
a second switch set, comprising the second switch and the fourth switch, wherein switches of the second switch set and the sixth and eighth switches are turned off during the first phase pulse and are turned on during the second phase pulse to make positive and negative terminals of a parallel branch formed by the first and second energy storage device connect to the second and first output terminals respectively.

4. The biphasic defibrillation circuit according to claim 3, wherein the first switch set comprises:
a first switch coupled between the first output terminal and positive lead that couples the first lead of the first energy storage device with the first lead of the second energy storage device;
a third switch coupled between a negative lead, that couples the second lead of the first energy storage device with the second lead of the second energy storage device, and the second output terminal of the switching circuit; and
wherein the second switch set comprises:
a second switch coupled between the positive lead and the second output terminal of the switching circuit; and
a fourth switch coupled between the negative lead and the first output terminal of the switching circuit.

5. The biphasic defibrillation circuit according to claim 1, further comprising:
a microprocessor for outputting control signals to the switching circuit; and
a transformer, wherein a primary coil of the transformer is coupled between power and ground through the fifth switch, and an auxiliary coil forms a charging structure which charges the first and second energy storage devices, wherein a control terminal of the fifth switch responds to a control signal from the microprocessor to change a state of the fifth switch between an off state and an on state.

6. The biphasic defibrillation circuit according to claim 1, wherein only the first energy storage device is used to deliver the first phase current to the defibrillation electrodes during the first phase pulse, and the first and second energy storage devices are connected in parallel to deliver the second phase current in the opposite direction to the first phase current to the defibrillation electrodes during the second phase pulse.

7. The biphasic defibrillation circuit according to claim 6, wherein the sixth switch and the seventh switch are turned off and the eighth switch is turned on during the first phase pulse and the sixth switch and the eighth switch are turned on while the seventh switch is turned off during the second phase pulse;
wherein a serial branch formed by the sixth switch and the second energy storage device connects to a serial branch formed by the eighth switch and the first energy storage device in parallel; and
wherein the switching circuit further comprises:
a first switch set, comprising the first switch and the third switch, wherein the first switch set is turned off during the second phase pulse and turned on during the first phase pulse to couple positive and negative terminals of the first energy storage device to the first and second output terminal of the switching circuit respectively; and
a second switch set, comprising the second switch and the fourth switch, wherein the second switch set is turned off during the first phase pulse and turned on during the second phase pulse to couple the positive and negative terminal of the parallel branch formed by the first and second energy storage device to the second and first output terminals of the switching circuit respectively.

8. The biphasic defibrillation circuit according to claim 1, wherein both the first and second energy storage devices are used to deliver the first phase current to the defibrillation electrodes during the first phase pulse, and only the first energy storage device is used to deliver the second phase current in the opposite direction to the first phase current to the defibrillation electrodes during the second phase pulse.

9. The biphasic defibrillation circuit according to claim 1, wherein the first and second energy storage devices are connected in a first combination to deliver the first phase current to the defibrillation electrodes during the first phase pulse, and the first and second energy storage devices are connected in a second combination to deliver the second phase current in the opposite direction of the first phase current to the defibrillation electrodes during the second phase pulse.

10. The biphasic defibrillation circuit according to claim 1, wherein at least one of the first and second energy storage devices comprises a capacitor.

11. The biphasic defibrillation circuit according to claim 1, wherein the voltage of the second energy storage device is one-tenth the voltage of the first energy storage device.

12. The biphasic defibrillation circuit according to claim 1, further comprising:
a first voltage sampling circuit coupled to two terminals of the serial branch formed by the first energy storage device and the eighth switch for sampling the voltage of the first energy storage device;
a second voltage sampling circuit coupled to positive and negative terminals of the second energy storage device for sampling the voltage of the second energy storage device.

13. The biphasic defibrillation circuit according to claim 1, further comprising:
a discharging circuit coupled between the second lead of the first energy storage device and the first lead of the second energy storage device for discharging excess energy stored in the first and second energy storage devices.

14. A biphasic defibrillation circuit for supplying first phase pulses and second phase pulses to a patient when connected to defibrillation electrodes of an automated external defibrillator, comprising:
- a switching circuit comprising an H-bridge switch arrangement, wherein a first output terminal and a second output terminal from the H-bridge switch arrangement are respectively coupled to the defibrillation electrodes, wherein the first phase pulse and the second phase pulse in an opposite direction to the first phase pulse are applied to the defibrillation electrodes by the switching circuit through changing the state of the switching circuit;
- a microprocessor for outputting control signals to the switching circuit and controlling the state of the switching circuit;
- a first energy storage device coupled to defibrillation electrodes by the switching circuit for delivering first phase current to the defibrillation electrodes during the first phase pulse and delivering second phase current to the defibrillation electrodes during the second phase pulse, wherein the first energy storage device is a high voltage energy storage device, a first lead of the first energy storage device is coupled with the switching circuit directly and a second lead of the first energy storage device is coupled with the switching circuit through a first switch; and
- a second energy storage device for delivering one or both of the first and second phase current to the defibrillation electrodes in combination with the first energy storage device, such that a discharging time constant of the second phase pulse is different from the discharging time constant of the first phase pulse or a starting discharging voltage of the second phase pulse is larger than an ending discharging voltage of the first phase pulse, wherein the second energy storage device is a low voltage energy storage device, a first lead of the second energy storage device is coupled with the switching circuitry through a second switch and with the second lead of the first energy storage device through a third switch and a second lead of the second energy storage device is coupled with the switching circuit directly, such that a serial branch formed by the second switch and the second energy storage device connects in parallel to a serial branch formed by the first energy storage device and the first switch,
- wherein a difference between a first length of a first discharging time of the first phase pulse and a second length of a second discharging time of the second phase pulse is less than 40 percent of the first length of the first discharging time.

15. An automated external defibrillator, comprising:
- a pair of defibrillation electrodes for connecting to a patient; and
- a biphasic defibrillation circuit comprising:
  - a switching circuit comprising a first output terminal and a second output terminal respectively coupled to the defibrillation electrodes, wherein the switching circuit includes a first switching set and a second switching set configured such that a first phase pulse and a second phase pulse in an opposite direction to the first phase pulse are applied to the defibrillation electrodes by the switching circuit;
  - a first energy storage device coupled to defibrillation electrodes by the switching circuit for delivering first phase current to the defibrillation electrodes during the first phase pulse and delivering second phase current in an opposite direction to the first phase current to the defibrillation electrodes during the second phase pulse, wherein the first energy storage device is a high voltage energy storage device, a first lead of the first energy storage device is coupled with the switching circuit directly and a second lead of the first energy storage device is coupled with the switching circuit through a first switch; and
  - a second energy storage device coupled to defibrillation electrodes during at least one of the first and second phase pulses for respectively delivering at least one of the first phase current and the second phase current in conjunction with the first energy storage device, wherein the second energy storage device is a low voltage energy storage device, a first lead of the second energy storage device is coupled with the switching circuitry through a second switch and with the second lead of the first energy storage device through a third switch and a second lead of the second energy storage device is coupled with the switching circuit directly, such that a serial branch formed by the second switch and the second energy storage device connects in parallel to a serial branch formed by the first energy storage device and the first switch,
  - wherein a difference between a trailing edge voltage of the first phase pulse and a leading edge voltage of the second phase pulse is less than 50 percent of the trailing edge voltage of the first phase pulse.

16. A biphasic defibrillation circuit for supplying a biphasic pulse to a patient when connected to defibrillation electrodes of an automated external defibrillator, comprising:
- a switching circuit comprising a first switch, a second switch, a third switch, and a fourth switch, wherein a first output terminal and a second output terminal from the switching circuit are respectively coupled to the defibrillation electrodes, wherein a first phase pulse and a second phase pulse in an opposite direction to the first phase pulse are applied to the defibrillation electrodes by the switching circuit;
- a first energy storage device coupled to the defibrillation electrodes by the switching circuit for delivering a first phase current to the defibrillation electrodes during the first phase pulse and delivering a second phase current in an opposite direction to the first phase current to the defibrillation electrodes during the second phase pulse, wherein the first energy storage device is a high voltage energy storage device, a first lead of the first energy storage device is coupled with the switching circuit directly and a second lead of the first energy storage device is coupled with the switching circuit through an eighth switch;
- a second energy storage device coupled to defibrillation electrodes during at least one of the first and second phase pulses for respectively delivering at least one of the first phase current and the second phase current in conjunction with the first energy storage device, wherein the second energy storage device is a low voltage energy storage device, a first lead of the second energy storage device is coupled with the switching circuitry through a sixth switch and with the second lead of the first energy storage device through a seventh switch and a second lead of the second energy storage device is coupled with the switching circuit directly; and
- a charging circuit coupled to the first and second energy storage devices for charging the first and second energy storage devices, wherein charging of the first and second energy storage devices is controlled by a fifth switch;

wherein a serial branch formed by the sixth switch and the second energy storage device connects in parallel to a serial branch formed by the first energy storage device and the eighth switch; and wherein a difference between a trailing edge voltage of the first phase pulse and a leading edge voltage of the second phase pulse is less than 50 percent of the trailing edge voltage of the first phase pulse.

* * * * *